United States Patent

Rittman, III et al.

(10) Patent No.: US 6,506,189 B1
(45) Date of Patent: Jan. 14, 2003

(54) COOL-TIP ELECTRODE THERMOSURGERY SYSTEM

(75) Inventors: William J. Rittman, III, Lynnfield; Eric R. Cosman, Belmont, both of MA (US)

(73) Assignee: Sherwood Services AG, Schaffhausen (CH)

(*) Notice: Subject to any disclaimer, the term of this patent is extended or adjusted under 35 U.S.C. 154(b) by 23 days.

(21) Appl. No.: 09/642,404

(22) Filed: Aug. 21, 2000

Related U.S. Application Data

(63) Continuation of application No. 08/634,005, filed on Apr. 15, 1996, now abandoned, which is a continuation-in-part of application No. 08/433,799, filed on May 4, 1995, now abandoned, and a continuation-in-part of application No. 08/562,986, filed on Nov. 24, 1995, now abandoned.

(51) Int. Cl.$^7$ .............................................. A61B 18/18
(52) U.S. Cl. ..................... 606/41; 607/102; 607/105; 606/49
(58) Field of Search .............................. 606/31, 41, 42, 606/48–50; 607/101–105; 600/374, 549

(56) References Cited

U.S. PATENT DOCUMENTS

| | | | |
|---|---|---|---|
| 4,411,266 A | * | 10/1983 | Cosman ...................... 600/549 |
| 4,565,200 A | | 1/1986 | Cosman |
| 4,576,177 A | | 3/1986 | Webster, Jr. |
| 4,608,977 A | | 9/1986 | Brown |
| 4,662,383 A | | 5/1987 | Sogawa et al. |
| 4,832,024 A | | 5/1989 | Boussignac et al. |
| 4,880,719 A | | 11/1989 | Murofushi et al. |
| 4,961,435 A | | 10/1990 | Kitagawa et al. |
| 4,966,597 A | | 10/1990 | Cosman |
| 4,993,430 A | | 2/1991 | Shimoyama et al. |
| 5,029,588 A | | 7/1991 | Yock et al. |
| 5,103,804 A | | 4/1992 | Abele et al. |

(List continued on next page.)

FOREIGN PATENT DOCUMENTS

| | | |
|---|---|---|
| DE | 2407559 | 2/1974 |
| EP | 0246350 A1 | 11/1987 |
| EP | 0310431 A2 | 4/1989 |
| EP | 0608609 A2 | 8/1994 |
| WO | WO 93/24066 | 12/1993 |
| WO | WO9428809 | 12/1994 |
| WO | WO 96/04860 | 2/1996 |
| WO | WO9618349 | 6/1996 |
| WO | WO 96/29946 A1 | 10/1996 |
| WO | WO 96/39914 | 12/1996 |
| WO | WO 97/06739 | 2/1997 |
| WO | WO 97/06740 | 2/1997 |
| WO | WO 97/06855 | 2/1997 |
| WO | WO 97/17029 | 5/1997 |

(List continued on next page.)

OTHER PUBLICATIONS

Cosman et al.: (1) "Theoretical Aspects of Radiofrequency Lesions in the Dorsal Root Entry Zone". *Neurosurgery* 15:945–950, 1984; (2) Cosman ER, Cosman BJ: "Methods of Making Nervous System Lesions", in William RH, Rengachary SS (eds): *Neurosurgery*. New York: McGraw–Hill, vol. 111, pp. 2490–2498, 1984.

(List continued on next page.)

*Primary Examiner*—Michael Peffley

(57) ABSTRACT

For heat ablating living tissue of a body, an ablation electrode, contacting a surface of the tissue or within tissue, is coupled to an RF power supply referenced to a second electrode contacting the body. Fluid coolant is circulated to cool the contact surface extending the ablation to an increased volume of tissue. Temperature may be sensed contiguous to the surface to control the flows of RF heating energy and fluid coolant. Computer capability implements control and provides graphics of data, preplans, or controls relative to the ablation. Several forms of electrode structures accommodate specific objectives.

17 Claims, 7 Drawing Sheets

U.S. PATENT DOCUMENTS

| | | | |
|---|---|---|---|
| 5,230,623 A | | 7/1993 | Guthrie et al. |
| 5,267,994 A | | 12/1993 | Gentelia et al. |
| 5,281,213 A | | 1/1994 | Milder et al. |
| 5,323,778 A | | 6/1994 | Kandarpa et al. |
| 5,330,518 A | | 7/1994 | Nielson et al. |
| 5,334,193 A | * | 8/1994 | Nardella ............... 606/41 |
| 5,342,357 A | | 8/1994 | Nardella |
| 5,348,554 A | * | 9/1994 | Imran et al. ............ 606/41 |
| 5,370,675 A | | 12/1994 | Edwards et al. |
| 5,383,876 A | | 1/1995 | Nardella |
| 5,383,917 A | | 1/1995 | Desai et al. |
| 5,385,148 A | | 1/1995 | Lesh et al. |
| 5,403,311 A | | 4/1995 | Abele et al. |
| 5,409,000 A | | 4/1995 | Imran |
| 5,409,006 A | | 4/1995 | Buchholtz et al. |
| 5,433,739 A | | 7/1995 | Sluijter et al. |
| 5,458,597 A | | 10/1995 | Edwards et al. |
| 5,462,521 A | | 10/1995 | Brucker et al. |
| 5,472,441 A | | 12/1995 | Edwards et al. |
| 5,490,850 A | | 2/1996 | Ellman et al. |
| 5,500,012 A | * | 3/1996 | Brucker et al. ......... 604/22 |
| 5,520,684 A | | 5/1996 | Imran |
| 5,536,267 A | | 7/1996 | Edwards et al. |
| 5,588,432 A | | 12/1996 | Crowley |
| 5,599,345 A | | 2/1997 | Edwards et al. |
| 5,647,871 A | | 7/1997 | Levine et al. |
| 5,688,267 A | * | 11/1997 | Panescu et al. ......... 606/31 |
| 5,868,740 A | | 2/1999 | LeVeen et al. |
| 5,921,982 A | | 7/1999 | Lesh et al. |
| 5,951,546 A | | 9/1999 | Lorentzen |
| 6,053,912 A | | 4/2000 | Panescu et al. |
| 6,241,725 B1 | | 6/2001 | Cosman |
| 6,337,998 B1 | | 1/2002 | Behl et al. |

OTHER PUBLICATIONS

*Nuclear Magnetic Resonance Imaging—Basic Principles*, Stuart W. Young, Raven Press, New York, 1984.

E.R. Cosman, et al., "Radiofrequency Lesion Generation and its Effect on Tissue Impedence", *Applied Neurophysiology*, 51:230–242, 1988.

*Modern Control Engineering*, by K. Ogata, Prentice–Hall, Englewood Cliffs, N.J., 1970.

E. Alexander et al., *J. Neurosurg.*, 83:271, 276, 1995.

Anderson, Gary et al., "A numerical study of rapid heating for high temperature radio frequency hyperthermia", International Journal of Bio–Medical Computing, 35 (1994) 297–307.

Goldberg, et al., "Tissue Ablation with Radiofrequency: Effective Probe Size, Gauge, Duration and Temperature and Lesion Volume ", *Acad Radio*, 1995, vol. 2, No. 5, pp. 399–404.

Melvin A. Astrahan, "A Localized Current Field Hyperthermia System for Use with 192–Iridium Interstitial Implants", *Medical Physics*, 9(3), May/Jun. 1982.

Anderson, Gary et al., "A numerical study of rapid heating for high temperature radio frequency hyperthermia", International Journal of Bio–Medical Computing, 35 (1994) 297–307.

* cited by examiner

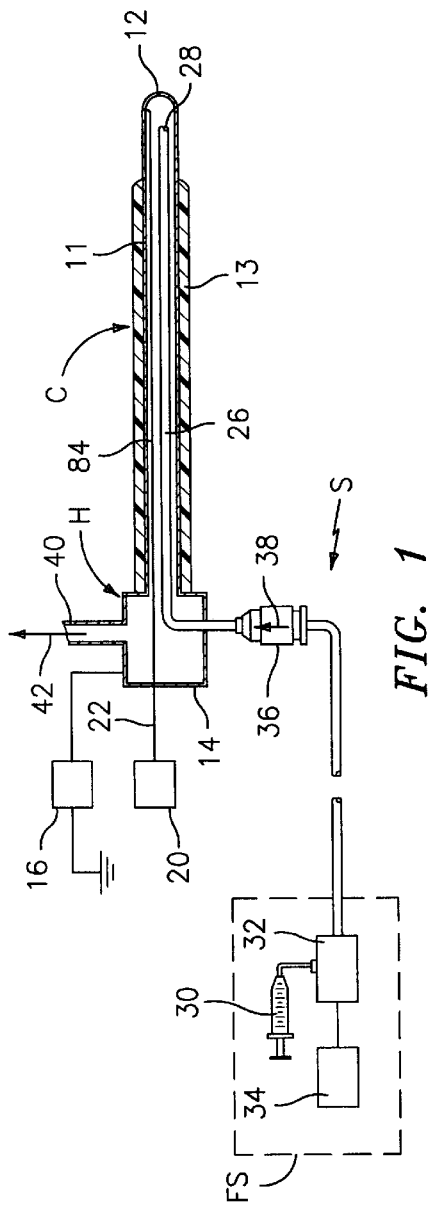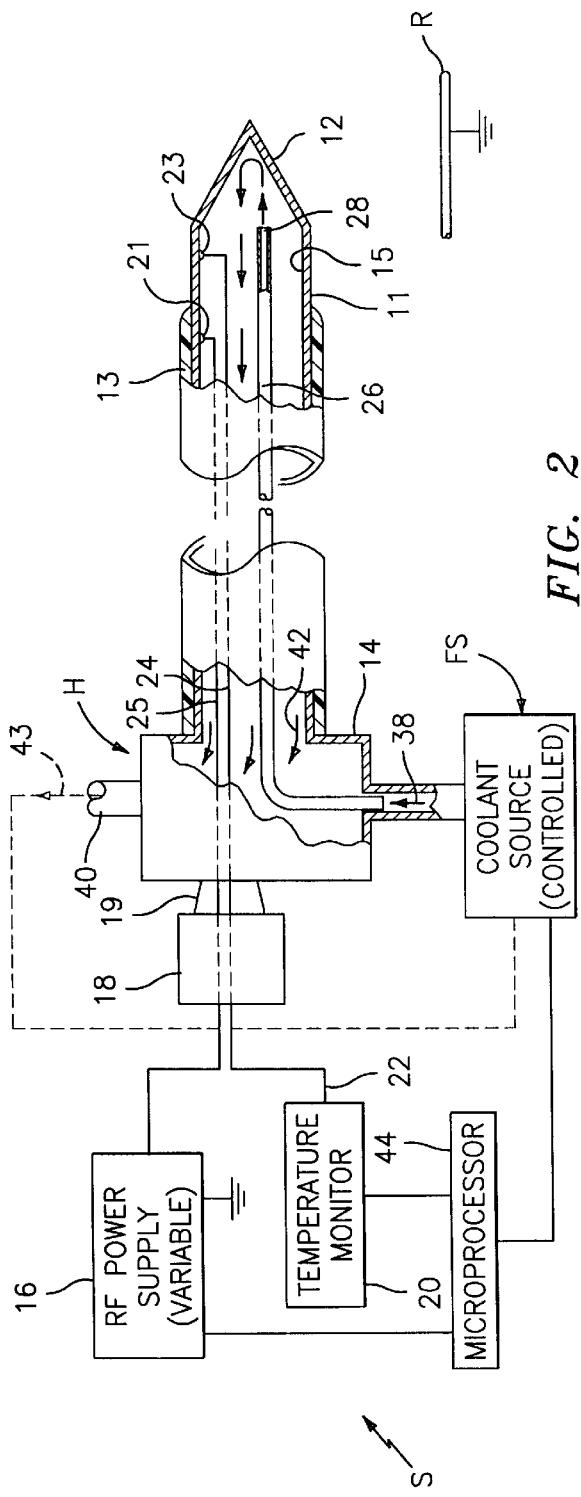

COOL-TIP ELECTRODE THERMOSURGERY SYSTEM

This is a continuation application of application Ser. No. 08/634,005, filed Apr. 15, 1996 (now abandoned), and a continuation-in-part of application Ser. No. 08/433,799, filed May 4, 1995 (now abandoned), and entitled "A Cooled Radio Frequency Electrode System For Heat Ablation In The Body," and application Ser. No. 08/562,986 (now abandoned), filed Nov. 24, 1995, and entitled "Cool-Tip Radiofrequency Thermosurgery Electrode System For Tumor Ablation."

BACKGROUND AND SUMMARY OF THE INVENTION

Therapeutic lesions in living bodies have been accomplished for many decades using radio-frequency (RF) and other forms of energy. The procedures have been particularly useful in the field of neurosurgery, typically where RF ablation electrodes (usually of elongated cylindrical geometry) are inserted into a living body. A typical form of such ablation electrodes incorporates an insulated sheath from which an exposed (uninsulated) tip extends.

Generally, the ablation electrode is coupled between a grounded RF power source (outside the body) and a reference ground or indifferent electrode for contacting a large surface of the body. When an RF voltage is provided between the reference electrode and the inserted ablation electrode, RF current flows from the ablation electrode through the body. Typically, the current density is very high near the tip of the ablation electrode, which heats and destroys the adjacent tissue.

Ablation electrode techniques, including the theory behind the techniques and many applications of the techniques are described in various papers, specifically see, (1) Cosman et al, "Theoretical Aspects of Radiofrequency Lesions in the Dorsal Root Entry Zone" *Neurosurg* 15:945–950, 1984 and (2) Cosman E. R. and Cosman B. J.: "Methods of Making Nervous System Lesions, in Wilkins R H, Rengachary S S (EDS): *Neurosurgery*, New York, McGraw-Hill, Vol. III, pp. 2490–2498, 1984.

In the past, RF ablation electrodes have incorporated temperature sensors, for example, in the form of a thermistor or thermocouple. In that regard, see U.S. Pat. No. 4,411,266 (1983, Eric R. Cosman). Typically, the sensor is connected to a monitoring apparatus for indicating temperature to assist in accomplishing a desired lesion. As generally known, for a given tip geometry and tip temperature, lesions of a prescribed size can be made quite consistently. In that regard also, see U.S. Pat. No. 4,411,266, (1983, Eric R. Cosman).

Over the years, a wide variety of RF electrode shapes and configurations have been used, for example, several current forms are available from Radionics, Inc., located in Burlington, Mass. Such electrodes have been used to accomplish lesions in a wide variety of targets within the body, including the brain, the spinal column and the heart.

However, a limitation of prior electrode ablation systems relates to the temperature of the tip. Specifically, prior ablation electrodes of a given tip geometry never should effectively exceed a temperature of 100° C. At that temperature, the surrounding tissue will boil and char. Also, uncontrolled disruption, such as hemorrhage and explosive gas formation, may cause extremely hazardous and clinically dangerous effects on the patient. Consequently, the lesion size for a given electrode geometry generally has been considered to be somewhat limited by the fact that the tissue near the tip must not exceed 100° C.

Essentially, during RF ablation, the electrode temperature is highest near the tip, because the current density is the highest at that location. Accordingly, temperature falls off as a function of distance from the electrode tip, and except for possible abnormalities in tissue conductivity and so on, in a somewhat predictable and even calculable pattern. As an attendant consequence, the size of RF lesions for a given electrode geometry have been somewhat limited.

One proposed solution to the limitation of lesion's size has been to employ "off-axis" electrodes, for example the so called Zervas Hypophysectomy Electrode or the Gildenberg Side-Outlet electrode, as manufactured by Radionics, Inc., Burlington, Mass. However, such systems in requiring multiple tissue punctures, increase the risk of hemorrhage, severely the prolong the time of surgery and increase the level of delicacy. Also, an umbrella of off-axis lesions may not produce a desired homogenous or uniform lesion. Accordingly, a need exists for an ablation electrode system capable of accomplishing enlarged lesions (radius and volume).

Considering lesion size, the papers of Cosman et al. (cited above) describe producing lesions in the brain of up to 10 to 12 millimeters by using very large electrodes. Yet, a need exists to attain much larger lesions. For example, in the liver, cancerous tumors may exceed 20 or 30 millimeters and may be clearly visible, as by tomographic scanning. Accordingly, a need exists for the capability to heat such tumors destructively with a minimum number of electrode insertions and heating episodes.

In general, the system of the present invention is directed to an improved system for accomplishing ablations in the body. The system offers a capability for controlled and modified temperature distribution as a function of distance from the ablation electrode so as to "throw out" or extend the heat to much larger distances while generally preserving the safety and control of the lesion process. The system enables controlling the temperature at a heating terminal, as for example the tip of an ablation electrode. For example, in disclosed embodiments, the temperature of the electrode tip (heat device) is controlled by incorporating a mechanism to cool the tip so as to reduce the excessive temperatures of the ablation process adjacent to the tip. For example, by the incorporation of a controllable, externally modulated agent (fluid) for secondary cooling of the tip, control is accomplished and in that regard, excessive heating of tissue near or adjacent the tip is reduced. Specifically, disclosed embodiments incorporate a cooling component which enables cooling of the ablation electrode and the tissue just adjacent to the electrode so as to modify the thermo distribution of heat disposition in the tissue and attain larger lesions. Essentially, the ablation energy dissipated in the tissue as heat can be effectively increased as a result of cooling at the working surface. As a result, the ablation volume is increased. Forms of cooled-tip, high frequency, electrodes as disclosed herein are well suited for percutaneous minimal invasive ablation of tumors. Specific embodiments are disclosed to be useful in thermo surgical settings which possess physical characteristics affording improved control and handling. Particular assemblies of cannula, fluid handling structures, irrigating and perfusion devices, radiofrequency cannula, and thermo probes are disclosed which afford the possibility of constructing various practical thermo-surgical applicators capable of effective operation. Additionally, as disclosed herein, control may be enhanced by the utilization of a computer, as with graphics and display capability to control, monitor or feedback parameters of the thermo surgery, also to preplan the ablation, or map, fuse or update images from one or more image scanners before, during or after the ablation process.

BRIEF DESCRIPTION OF THE DRAWINGS

In the drawings, which constitute a part of the specification, exemplary embodiments exhibiting various objectives and features hereof are set forth, specifically:

FIG. 1 is a block and sectional diagram of a system constructed in accordance with the present invention;

FIG. 2 is a fragmentary enlarged block and sectional diagram illustrating portions of the system of FIG. 1 in greater structural detail with slight modification;

DESCRIPTION OF THE INVENTION

Figure 2A:
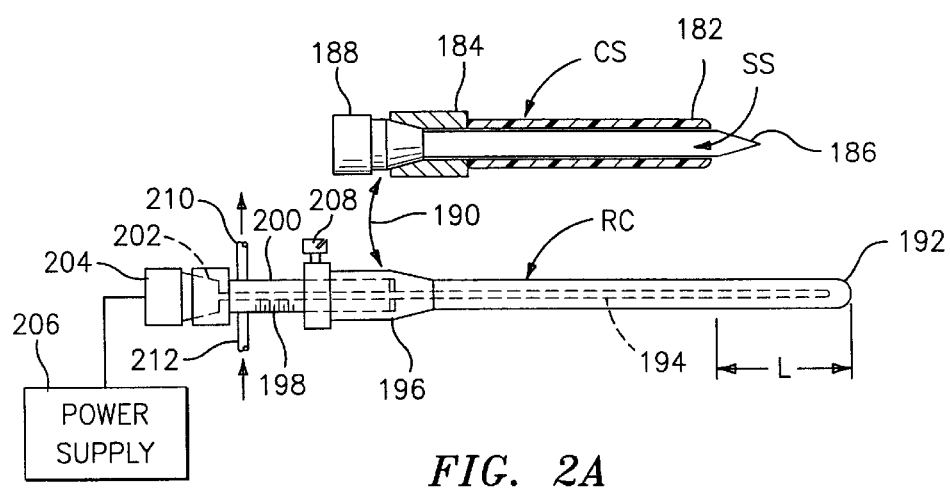
FIG. 2A is a sectional and elevational view of disengaged components representative of an alternative embodiment in accordance with the present invention.

The following embodiments illustrate and exemplify the present invention and concepts thereof, yet in that regard, they are deemed to afford the best embodiments for purposes of disclosure and to provide a basis for the claims herein which define the scope of the present invention.

Referring somewhat concurrently to FIGS. 1 and 2, the illustrated ablation system generally incorporates an elongate shaft or cannula body C for insertion, either percutaneously or intraoperatively into an open wound site. As illustrated the cannula body C is integral with a head or hub element H coupled to remote support components, collectively designated S.

Structurally, the cannula body C incorporates an elongated hollow ablative electrode 11 (FIG. 2) formed of conductive material, e.g. metal such as stainless steel, titanium, etc. At the distal end of the cannula body C, the electrode 11 defines a tip 12 which may be radiused at its end or which may be pointed. In one form, the tip 12 may define a trocar point and may be of robust metal construction to facilitate insertion or penetration of tissue. In operation when using an R.F. power supply 16, electrical current spreads from the tip 12 to pass through the surrounding tissue causing the tissue to heat up. That is, when the tip 12 is positioned contiguous (near, touching or within) to a tissue, energy from the R.F. power supply 16 is dissipated into heat within the tissue.

Over most of its length, the electrode 11 carries an insulative coating 13 for selectively preventing the flow of electrical current from the shaft 15 of electrode 11 into surrounding tissue. Thus, the insulative coating 13 shields the intervening tissue from RF current, so that such tissue is not substantially heated along the length of the shaft 15 except by the heating effect from the exposed tip 12.

The proximal end (left) of the electrode 11 (FIG. 2) is integral with an enlarged housing 14 of the hub H which carries electrical and coolant connections as explained in greater detail below. Outside the patient's body, the housing 14 is of cylindrical configuration, defining ports for connections to the support components S, i.e., electrical and fluid couplings. As suggested, the housing 14 may be integral with the electrode 11, formed of metal, or it may constitute a separate subassembly as described below. Alternatively, the housing 14 can be of plastic, accommodating separate electrical connections. In that regard, a plastic housing 14 is amenable to low artifact imaging by X-rays CT, MRI, etc. as may be desirable in some situations.

The housing 14 mates with a block 18 (FIG. 2) defining a luer taper lock 19 sealing the block 18 to the housing 14. Thus, fluid and electrical couplings are provided. Specifically, connection to a regulated RF supply 16 (variable) can take the form of a standard cable connector, a leader wire, a jack-type contact or other designs known in the high frequency art. The temperature-sensing and radiofrequency electrical connections can be made through the housing 14 and extend to the region of the tip 12, where an RF line 25 is connected by junction 21 (a weld, braze, or other secure electrical connection). With sensor lines 24 extending to a thermo-sensor 23, as in the form of a thermistor, or a thermocouple, or other type of sensor, the thermo sensor 23 may be fused or in thermal contact with the wall of the tip 12 to sense the temperature of the tip 12.

Recapitulating, the RF power supply 16 may be referenced to reference potential as illustrated (FIG. 2), and coupled through the block 18 affixed to the hub H. Specifically, the RF power supply 16 provides RF voltage through the block 18 with an electrical connection to the electrode 11 as indicated by the line 25, to the connection junction 21. The power supply 16 may take the form of an RF generator as exemplified by the RFG-3C RF Lesion Generator System available from Radionics, Inc., Burlington, Mass.

As indicated above and in accordance with common practice, when the ablation electrode 11 is in a patient's body, an electrical circuit is completed through the body to a reference or dispersive electrode R (symbolically represented in FIG. 2) that is connected elsewhere to the body. Consequently the RF power supply 16 heats body tissue by current from the tip 12. In that regard, a temperature monitor 20 (FIG. 2 left, center) may be electrically connected by lines 22 and 24 to a temperature sensor 23 as in the form of a thermocouple or thermistor typically within or contacting the tip 12. As illustrated, the sensor 23 is connected to the tip 12. The sensed temperature may be utilized to control either or both of the flow of RF energy or the flow of coolant to attain the desired ablation while maintaining the maximum temperature substantially below 100° C. Note that a plurality of sensors could be utilized including units extending outside the tip 12 to measure temperatures existing at various locations in the proximity of the tip 12. The temperature monitor 20 may be as exemplified by the TC thermocouple temperature monitoring devices available from; Radionics, Inc., Burlington, Mass.

In accordance herewith, temperatures at, or near the tip 12 (manifest by the monitor 20) may be controlled by controlling the flow of fluid coolant through the ablation electrode 11. Accordingly, the temperature of the tissue contacting or near the tip 12 is controlled. In the disclosed embodiment, fluid from a fluid source FS is carried the length of the ablation electrode 11 (FIG. 2) through a tube 26 extending from the housing H to the distal end of the electrode 11 terminating in an open end 28 at the tip 12. At the opposite end of the electrode 11, within the housing H, the tube 26 is connected to receive fluid. As illustrated in the detailed structure of FIG. 1, the fluid source FS includes a source unit 34 coupled through a control 32 utilizing a hypodermic syringe 30 to actuate fluid flow (arrow 38) through a coupling 38. Thus, fluid flow is regulated in accordance with observed temperature, allowing increased flow of RF energy.

The fluid coolant may take the form of water or saline for the convection removal of heat from the tip 12. The reservoir or source unit 34 (FIG. 1) might be a large reservoir of cooled water, saline or other fluid. As a simplistic example, a tank of water with ice cubes can function to maintain the coolant at a temperature of approximately 0° C. As another example, the fluid source FS could incorporate a peristaltic pump or other fluid pump, or could merely be a gravity feed for supplying fluid from a bag or rigid tank.

Flow away from the tip 12 is back to the hub H (FIG. 2) to exit the hub H through an exit port 40 as illustrated by arrows 42 and 43. Note that the ports may take the form of simple couplings, rigid units or may comprise flexible tubular couplings to reduce torque transmission to the electrode 11. Also, the coolant flow members may simply take the form of PVC tubes with plastic luer connectors for ease of use.

As a result of the coolant flow, the interior of the electrode 11, in particular the electrode tip 12, can be held to a temperature near that of the fluid source FS. The coolant can circulate in a closed system as illustrated in FIG. 2. Also, in some situations, it may be desirable to reverse the direction of fluid flow from that depicted in the figures. As treated in detail below, coordinated operation, involving RF heating along with the cooling may be accomplished by a microprocessor 44 (FIG. 2). In that regard, the microprocessor 44 is coupled to the RF power supply 16, the temperature monitor 20 and the fluid source FS to receive data on flow rates and temperatures and exercise control. Accordingly, an integrated operation is provided with feedback from the temperature monitor 20 in a controlled format and various functions can be concurrently accomplished. Thus, facilitated by the cooling, the ablation electrode 11 is moderated, changed, controlled or stabilized. Such controlled operation can effectively reduce the temperature of tissue near the tip 12 to accomplish an equilibrium temperature distribution tailored to the desired size of the desired lesion.

The temperature distribution in the tissue near the tip 12 depends on the RF current from the tip 12 and depends on the temperature of the tissue which is adjacent to the tip 12 and that tip temperature can be controlled to approach the temperature of the fluid from the source FS. Thus, a thermal boundary condition is established, holding the temperature of the tissue (near the tip 12) to approximately the temperature of the tip itself, e.g. the temperature of the fluid inside the tip 12. Accordingly, by temperature control, a surgeon may impose a defined temperature at the boundary of the electrode tip 12 which can be somewhat independent of the RF heating process and in fact, dramatically modify the temperature distribution in the tissue.

To consider temperature distributions from the tip 12, reference now will be made to the graph of FIG. 3. The nominal radial distance R from the central axis of an electrode tip is plotted against temperature T. In the illustrated example, a nominal radius $R_0$ of the tip is depicted. A body temperature of 37° C. is the base reference line in the graph. Also, a temperature level of 100° C. is indicated; the boiling point of water and essentially that of body tissue. As explained above, such a temperature is highly undesirable in any controlled clinical setting. Accordingly, it is important to maintain the temperature of the electrode substantially below 100° C.

Figure 3:
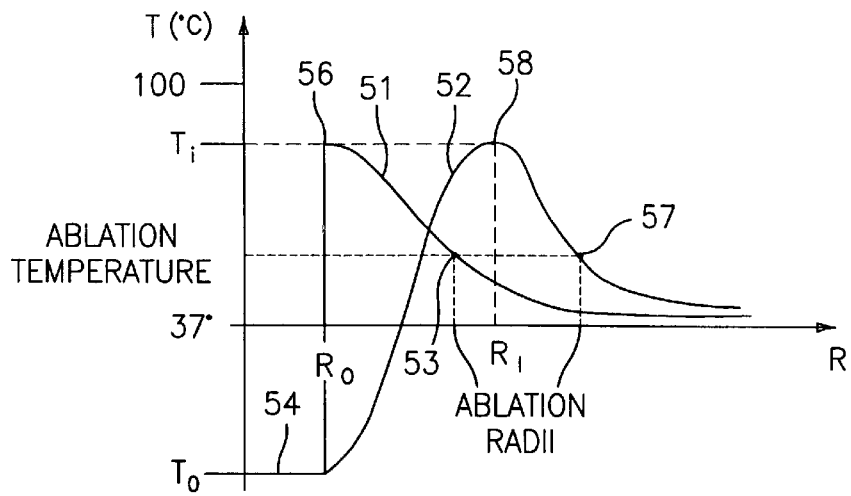
FIG. 3 is a rectangular coordinate graph illustrating temperature distributions associated with RF electrodes.

Generally, the curves of FIG. 3 illustrate somewhat idealized characteristics of exemplary electrodes, indicating tissue temperature T as a function of distance R from the electrode. Though idealized, the curves are calculable and can serve to indicate lesion size. In that regard, see the papers identified above, Cosman et al. (both 1984).

The curve 51 represents the operation of a traditional ablation electrode, whereby at the electrode surface ($R_0$) the tissue is elevated to a safe temperature $T_1$. However, from that location, the temperature rapidly falls off and approaches body temperature (37° C.) asymptotically as the distance R increases from the electrode.

It is generally accepted that most bodily tissue across most cell lines will permanently die if held at a temperature in the range of 45° C. to 60° C. for a sustained period, e.g. 60 seconds. Accordingly, the ablation radius for a lesion generally corresponds to the radius associated with temperatures in a range of 45° C. to 60° C. Thus, ablation by the electrode as depicted by the curve 51 would be effective only to the radius of a point 53.

The curve 52 illustrates the characteristic of an electrode or ablation system in accordance with the present invention. The improved electrode (e.g. electrode 11, FIG. 2) can be maintained at an approximate temperature, e.g. temperature $T_0$, as indicated, substantially lower than the body temperature of 37° C. In FIG. 3, the representation is that the temperature $T_0$ can approach 0° C., the freezing point of water. Of course, it is not necessary to employ such a low temperature; however, the graph of FIG. 3 is illustrative. Consequently, a substantially horizontal section 54 of the curve 52 indicates a constant temperature $T_0$ within the radius $R_0$. The section 54 represents a situation in which the interior of the improved electrode tip is held at a temperature $T_0$ by circulating coolant. Such operation imposes the boundary condition at $R_0$ such that the tissue outside the tip is also substantially at the temperature $T_0$.

Considering further representations of the curve 52, the RF current causes energy dissipation in the tissue immediately adjacent to and distanced from the electrode radius $R_0$, but the equilibrium temperature distribution of the tissue is controlled by the equation of heat disposition, conduction and convection throughout the space. The fact that the improved electrode tip (tip 12, FIG. 2) is held at the temperature $T_0$ means that the temperature curve 52 must be continuous and meet the point $T_0$ at radius $R_0$. As a result, the heating causes higher temperatures at greater distances from the tip as shown by the rise of the curve 52 to a maximum temperature $T_1$ at a radius $R_1$ substantially greater than the radius $R_0$. The actual ablation radius is indicated at a point 57, substantially displaced from the point 53.

Beyond the radius $R_1$, blood convection dominates to a larger radius and as illustrated, the curve 52 falls off to its asymptotic limit approximating 37° C.

The curve 52 illustrates that by cooling in the improved electrode tip, the radius $R_1$ corresponding to a temperature $T_1$ is much larger than the radius corresponding to the same temperature $T_1$ for traditional electrodes. In essence, by cooling the electrode tip, the zone of highest temperature is "thrown out" or extended to a larger radius, in the illustrated case to a radius $R_1$, further away from the electrode than the radius $R_0$ of traditional electrodes; similarly the ablation radii as indicated by the points 53 and 57.

Summarily, the consequence of the larger radius of elevated temperature is a larger kill radius. That is, the kill radius or volume of the ablation zone can be made substantially larger for a cooled electrode of essentially identical geometry. This may be illustrated by the radius for the point 57 on the curve 52 compared to the point 53 on the curve 51. As a consequence, a quantum leap is represented in the capability of making RF lesions and in making larger lesions with greater control for a particular electrode geometry. Implementations in accordance with the disclosed embodiments in actual living tissue, indicate that with an electrode of 20 gauge (a radius of under 1 mm) lesion sizes can be expanded from a limited range of approximately 10 mm in diameter to diameters of 20 to 30 mm. The consequences are considerable.

In a clinical setting, systems hereof offer a very material advantage. For example, for a tumor volume in the range of 20 mm or more, a single electrode can be used to engulf the volume in a lethal temperature zone. Conversely, with traditional electrodes, multiple passes or multiple off-access electrode passes would be required with all of the incumbent disadvantages and hazards of hemorrhage, discomfort, risk of hitting critical structures, inhomogeneities of temperature distributions, and the risk of not ablating the entire volume of concern. Thus, in accordance herewith, significant clinical advantages are offered in the ablation of tissue volumes.

From the above description, it will be apparent to persons skilled in the art that the present invention may be embodied in a number of various forms. In that regard, the embodiment of FIGS. 1 and 2 may be implemented variously, for example to be either disposable or non-disposable. The thermal circulation system may or may not be an intact closed end, tissue-penetrating structure. Temperature sensors and monitors may or may not be used in the electrode or applicator.

By providing the temperature sensor 24 in a removable form, its failure will rot likely compromise the specific operation of the cannula body C. Generally, modulization may involve separate units involving the heating, cooling and sensing operations to enable separate and distinct reusability or disposability.

Various forms of plastics, metals and composite materials may be utilized to accomplish specific objectives. For example, the insulation coating 13 may take the form of Teflon, polyethylene, and so on as has been utilized in past electrode designs available from Radionics, Burlington, Mass.

Turning now to specific alternative forms, FIG. 2A illustrates a dual component structure. At the top, a cannula sheath CS is illustrated telescopically receiving an occluding stylet shaft SS, the two being mated for placement, as in body tissue. Subsequently, the procedure involves removing the stylet shaft SS from the cannula sheath CS and inserting a cooled RF cannula RC as illustrated separately. Accordingly, somewhat greater flexibility of operation is attained.

The cannula shaft CS may incorporate an elongated tubular insulated structure (for example in the form of a plastic sheath or insulation coating a metal tube) 182 affixed to a hub 184. Generally, the insulated structure 182 constitutes an electrically insulating substance as a surface while the hub 184 may be either metal or plastic; the latter possibly of a low radiopacity material that is desirable for position confirmation by x-ray, CT, MRI and so on.

The stylet shaft SS is loosely received within the insulated structure 182 for free telescopic movement, and may have a pointed tip 186 which may be a trocar, conical, bevel or other penetrating shape for introducing the noted combination into a patient's body. During insertion, the hub 184 mates with the block 188 to lock and seal the cannula sheath CS with the stylet shaft SS for effective insertion.

Once the combination or composite cannula sheath CS and stylet shaft SS are appropriately positioned within the tissue, the stylet shaft SS is withdrawn and the cooled cannula RC is introduced. Accordingly, as indicated by the double ended arrow 190, the positions of the stylet shaft SS and the cooled RF cannula RC are reversed from that illustrated. With the cooled cannula RC received in the cannula sheath CS, a tip 192 extends from the insulation 182 by the lengths L as indicated. Accordingly, the unit is mobilized for effective heat ablation.

Considering the cooled cannula RC in somewhat greater detail, both heating and cooling capabilities are provided as described with respect to earlier embodiments. In that regard, full details of the cooled RF cannula RC are not repeated in FIG. 2A. Rather, component parts are generally indicated. Specifically, from the tip 192, the hollow electrode 194 (of substantially uniform section) continues (left) to mate with a sizing clamp 196 accommodating various lengths in accordance with well known structures. That is, with a traditional sizing clamp 196, the length L of the extending tip 192 can be varied to accommodate specific desired objectives. The sizing clamp 196 is secured by a lock screw 208.

In using the structure of FIG. 2A, a measure of the effective tip length (degree of extension L) is indicated by scale markings 198 on a cylindrical portion 200 (left) extending from the sizing clamp 196. Remote from the clamp 196, the portion 200 engages a coupling 202, which in turn receives a connector block 204 which carries an electrical connection 194 from the electrode tip 192 or cannula RC to a source 206 of RF power as explained above with respect to FIG. 2.

Coolant, to be circulated through the tip 192, is provided through tubes 210 and 212. Thus, as described in detail with respect to FIGS. 1 and 2, the tubes 210 and 212 accommodate the passage of coolant fluid through the RF/cooling cannula RC to the tip 192 thereby cooling the tip or "clamping" it to the desired temperature, which may be below 37° C. Accordingly, as explained above, the structure "throws" the temperature distribution outward to achieve a larger ablation volume.

Figure 2B:
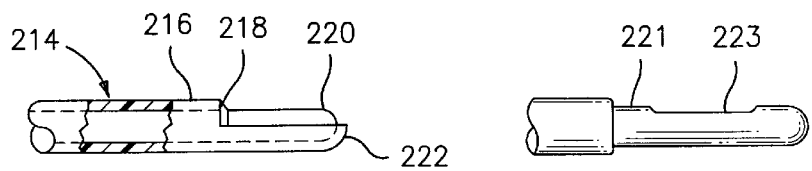
FIG. 2B is a fragmentary view showing another alternative embodiment from that of FIG. 2A.
Figure 2C:
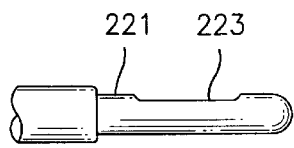
FIG. 2C is a fragmentary view showing still another alternative embodiment from that of FIG. 2A.

FIG. 2B is slightly enlarged and shows a modification of FIG. 2A. Specifically, a directional electrode 214 of FIG. 2B has an insulated sheath 216; however, the full annulus of the sheath 216 terminates at a belt 218. From the belt 218, the sheath 216 covers only one half of the electrode tip 220 in the form of an elongate half dome extension 222. Accordingly, an exposed conductive surface of the tip 220 (somewhat an arcuate half cylindrical surface) is illustrated at the top of the tip while the other half of the tip is insulated to block the emanation of RF current. As a consequence, the RF current emanates directionally into the tissue and accordingly ablation is directional. Thus, the tissue is heated at a "window" in the insulation by the exposed-tip (upper) side of the tip 220 but not on the opposite insulation shielded side (lower). Using the embodiment of FIG. 2B, non symmetrical lesions are possible.

Another variation is illustrated by the fragmentary modified view of FIG. 2C, again, a variation of the structure as illustrated in FIG. 2A. The tip 221 has a side window 223 to function as described with reference to FIG. 2B with the tip end covered, or in part covered. The variation may be useful as a biopsy needle, an aspirating device, a suction tube device, a side-scanning ultrasonic detector or a radar system, for example where biopsies, aspirations, etc. can be taken through the window 223. Such side-cutting or windowed type biopsy needles are known in the industry as represented by the NBA Nashhold biopsy needle as produced by Radionics, Inc., Burlington, Mass.

Figure 2D:
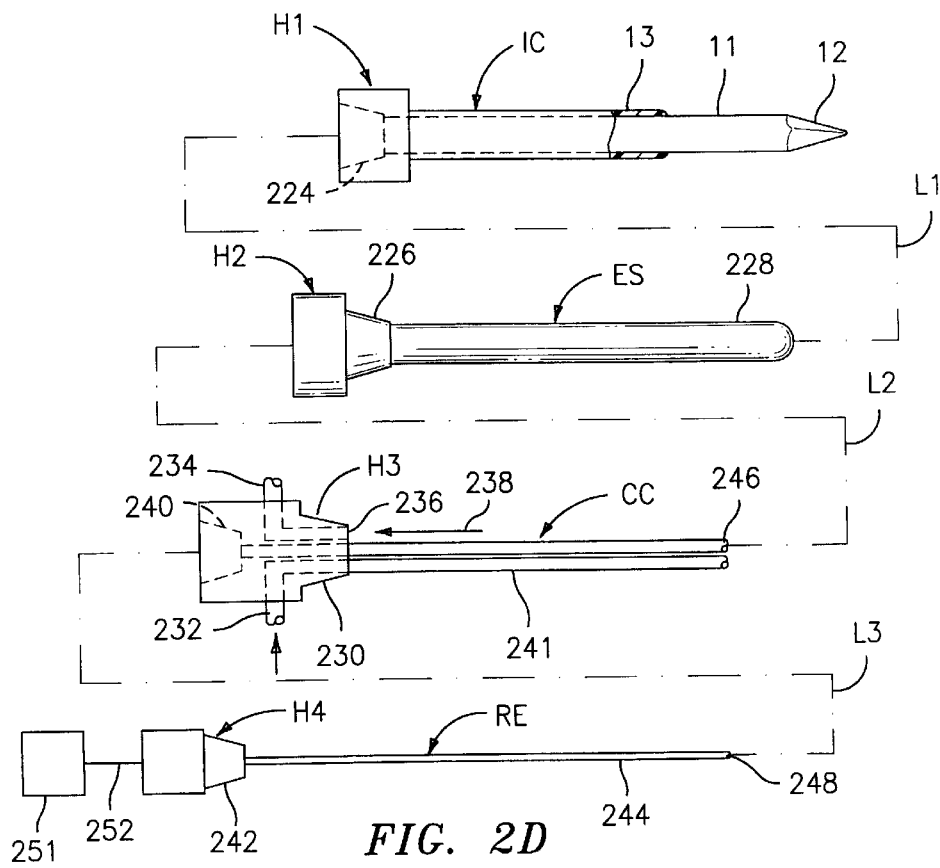
FIG. 2D is a sectional and elevation view of unassembled components of one other alternative form of the electrode component of the system of FIG. 2.

Still another variation of the system as depicted in FIGS. 1 and 2 is illustrated in FIG. 2D. Essentially, the structure of FIG. 2D involves four separate components (separately illustrated) that are sequentially mated to accomplish an ablation. Specifically, as indicated by dashed lines L1, L2 and L3, the interrelated components are telescopically mated to accomplish an integrated system.

Basically, an insulated cannula IC (top) receives an electrode stylet ES which then in turn receives a coolant cannula CC, and which in turn receives a RF element RE. Although the component parts are somewhat similar to parts as described above, they are distinct as will now be described. However, to the extent appropriate, similar reference numerals are employed.

An ablation electrode 11 (FIG. 2D upper right) which can be coupled to an RF source (not shown) defines a pointed tip 12 extending from an insulation coating 13 that covers the electrode 11 away from the tip to a hub H1. As previously explained, the tip 12, enables penetration.

Remote from the tip 12, the hub H1 (FIG. 2D) as the other hubs of FIG. 2D, may comprise various materials including metal or plastic and defines a female luer shape 224 (dash line) coaxial with the electrode 11 to lockingly receive a male member. Specifically, as illustrated the female shape 224 of the hub H1 receives the male luer shape 226 of a hub H2, a part of the electrode stylet ES.

With the insulated cannula IC positioned in tissue, the electrode stylet ES is telescopically inserted so that an elongate coaxial stylet 228 extends substantially the length of the hollow electrode 11. The lockingly engaged members provide a somewhat stiffer structure for effective manipulation and penetration of tissue or passage into bodily openings.

With the composite (the insulated cannula IC and the electrode stylet ES) matingly engaged and placed, a coolant cannula CC is placed in the stylet ES. The coolant cannula CC incorporates a hub H3 defining a male luer shape 230 for locking the entire assembly telescopically within the stylet 228 during the interval of heat ablation.

Considering the structure in greater detail, the hub H3 defines axially parallel passages for accommodating the flow of coolant. A radially-extending tube 232 enters the hub H3 (bottom) to provide a coolant flow passage from the hub H3 to a coolant tube 241 extending substantially the length of the stylet 228.

Another fluid passage 234 (top) passing through the hub H3 turns axially from a port 236 to accommodate the exit flow of coolant as indicated by the arrow 238. Accordingly, coolant is received through a tube 232, travels the length of the unit and emerges from the tube 234. As a consequence, cooling is accomplished in accordance herewith.

The hub H3 also defines a coaxial luer opening 240 for mating engagement with a male luer shape 242 in a hub H4 of the RF element RE (FIG. 2D bottom). Accordingly, the element RE can be inserted so that an elongated sensing element 244 is coaxially received in the elongate tube 246 of the coolant cannula CC. Accordingly, an end 248 of the element RE is positioned at the distal tip of the tube 246. The tip 248 (RF element RE) may incorporate a thermo sensor to detect the coolant fluid temperature, or it may be adapted to contact the wall of the tip 12 so as to detect the tissue temperature nearby. The hub H4 has a male luer lock 242 to seal with the female luer opening 240. Also, through the hub H4, the element RE connects to an external electrical unit 251 by a cable 250, as described in other embodiments; the unit 251 for example being a power supply for electrical current or other energy source to produce heating in the tissue near the tip 12.

The system of FIG. 2D can be embodied in a simpler form. For instance, the insulated cannula IC, if sufficiently stiff may not require the stylet 228 for penetration. The coolant cannula CC may employ only a single channel such as the tube 241 for fluid circulation without the tube 246. The connection to the power supply 251 may be made directly to the hub H3 and thus to the tip 12 without separate RF element RE.

Figure 4:
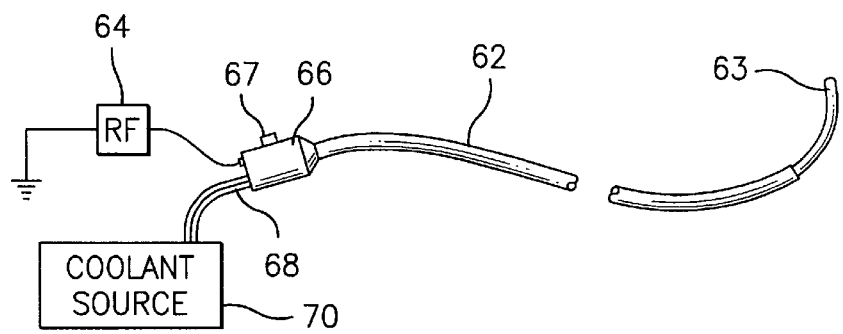
FIG. 4 is a block and schematic diagram of an alternative form of a system in accordance with the present inventions

Turning now to other embodiments more distinct from the structure of FIG. 2, FIG. 4 shows a flexible electrode which incorporates a cooled tip as disclosed above. Specifically, the electrode 62 is elongated and insulated over most of its length. The electrode 62 could take the form of a catheter formed of plastic, a spiral wound or braided structure, or various other flexible tube configuration of insulating an and non-insulating material.

Essentially, the electrode 62 defines a flexible, hollow, externally insulated structure terminated at its distal end in a tip 63 with a conductive surface. Utilizing techniques well known in the art, the electrode 62 may incorporate control elements to attain various curvatures. In that regard, the curvature of the electrode 62 (as well as the tip 63) can be controlled at a hub 66 by utilizing a control 67 that may be variously implemented as a lever, button or knob. That is, in accordance with prior technology, the control 67 is connected to mechanisms within the electrode 62, as by push-pull wires to control the degree of curvature, the direction of curvature or the position. As indicated, such mechanisms are known and utilized in the field of cardiac electrode physiology as well as endoscopy for targetry throughout the body.

The electrode 62 further incorporates electrical conduction means and fluid flow means internally mounted as described above with respect to FIGS. 1 and 2. Accordingly, RF power is provided from a power supply 64 so as to provide ablation heat as described above. Also as described above, conduits 68 supply a stream of fluid coolant from a source 70. Just as in the structures described above, the coolant is channeled to the tip 63 to cool the tip.

The structure of FIG. 4 may be particularly useful for cardiac ablation. Generally, cardiac ablation catheters are well known; however, the improved form of the present invention offers enhanced possibilities. Incidentally, forms of flexible electrodes as disclosed with respect to FIG. 4 also may incorporate or include side-outlet electrodes as for example the Zervas type; however, with cooled tips as described herein.

Figure 5:
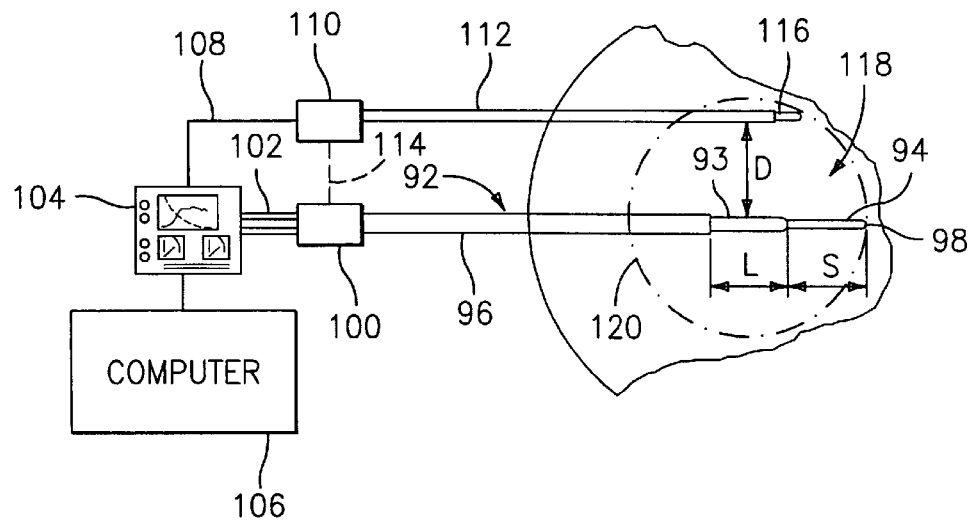
FIG. 5 is a block and elevation of still another alternative form of the present invention.

FIG. 5 shows an embodiment of the present invention including a satellite temperature monitoring electrode(s) used to monitor the size of a lesion, specifically in terms of volume or distance away from the lesion marking tip. A main electrode shaft 92 is constructed somewhat in accordance with the previously described embodiments. Specifically, a hollow electrode 92 carries an insulating coating 96 and has an exposed tip 93 as previously disclosed, and also is similar to the structure of FIGS. 1 and 2 with respect to heating and cooling. However, an extension tip 94 extends from the distal end of the electrode tip 93, and it may contain a thermosensor at or near its end 98 which has similar structure to the sensor 23 and a related connection line 24 (e.g. cable) as shown in FIG. 2. Accordingly, the distal end of the shaft 92 (FIG. 5) is terminated by an exposed length L of the electrode tip 93, and the extension 94 may sense ablation heating at a distance S from the tip 93, this giving added control to the ablation. Thus, the shaft 92 incorporating the electrode tip 93 (along with the interior cooling and heating members) is generally similar to the cannula C (FIG. 2). The shaft extension distance S may be varied or set by the operator as by structures similar to that in FIG. 2A for adjusting tip exposure L. Shaft extension 94 may have similar structures to that of FIG. 2 and also may contain heating and cooling members.

Somewhat similar to previously described embodiments, the electrode shaft 92 of FIG. 5 is affixed to a hub 100 affording connection through a pair of couplings 102 to a controller unit 104 and an ancillary computer system 106. Detailed forms of the computer control and display structures are described with reference to later embodiments herein.

From the controller unit 104, a cable 108 extends to a secondary hub 110 carrying a secondary probe 112 which will enable ancillary thermosensing (or, heating or cooling) at a position near the tip 116 offset at a distance D from electrode tip 93. Recapitulating, the shaft 92 affords a controlled heating structure along with the capability to monitor temperature along the length of the extension 98. The secondary probe 112 is offset by a fixed distance D (see line 114 representing a mechanical connection or an insertion separation of shafts 92 and 112 with respect to tissue placement) Accordingly, based on readings of temperature, power, voltage, current, and/or other lesioning parameters (as well as the cooling), control is by the control unit 104 in combination with the computer 106. In that regard, as illustrated, displays 114 are provided by the control unit 104 that may include graphic images and meter indications.

As an aid to control, the probe 112 may be coated with insulation material so as not to perturb substantially the flow of current from the tip 93. The probe has a sensor 116 at its tip to indicate temperature in the tissue as generally indicated by the arrow 118.

As heating by the structure of FIG. 5 proceeds, an isotherm or region of constant temperature develops, as represented by a dashed line 120 which represents a surface of constant temperature within the tissue. Again, by monitoring the temperatures at various locations (as at tips 116, 98, and 93), a quantitative indication of the lesion size can be determined. Such information can be displayed, monitored, and/or controlled (as by controller 104 and computer 106), and as indicated and automatic control can be implemented.

Figure 6:
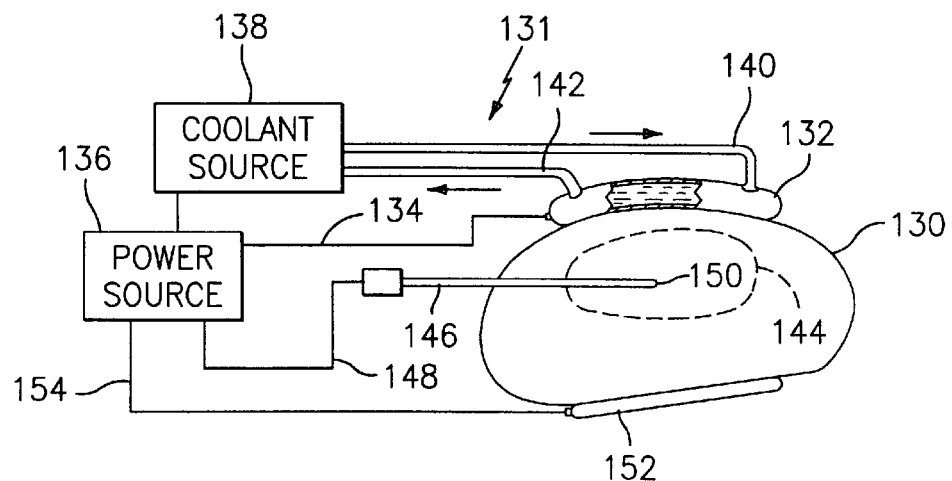
FIG. 6 is a block and elevation view of still another alternative form of the present invention.

FIG. 6 shows another embodiment of the present invention incorporating surface/mounted electrodes. Such structures are suited to the ablation of certain specific anatomy. For example, a portion 130 of anatomy is depicted to contain a tumor to be destroyed. The active electrode system 131 as illustrated incorporates a flat-area ablation electrode or ablation applicator 132 shown in contact with the body portion 130. The electrode 132 takes the form of a plate-like configuration formed of metal mesh. Alternatively, the electrode 132 may take the form of a balloon or bag-like structure incorporating an electrically conductive mesh, wire or surface material to accommodate a good RF contact with the body portion 130.

The ablation electrode 132 is coupled through an RF cable 134 to a power source 136. As alternatives, the source 136 might take the form of a microwave, laser, ultrasound, or other direct or alternating current power source, and accordingly connection 134 is a conveyor of that energy from source 136, so that ablation energy is provided from the electrode 132 to the body portion 130. As illustrated in FIG. 6,: the electrode 132 also is coupled to a coolant source 138 which may take any of the forms indicated herein for supplying coolant to the electrode 132 through passages 140 and 142.

Assume for example, a desire to accomplish a lesion volume of isotherms in the tissue portion 130 as indicated by the dashed line loop 144. In that regard, a temperature measuring satellite sensor 146 is depicted extending into the loop 144. As illustrated, the sensor 146 is electrically coupled through a cable 148 to the source 136. Accordingly, a tip 150 of the sensor 146 provides pertinent temperature indications to the source 136 for controlling the passage of electrical energy to the electrode 132 as well as the flow of coolant from the source 138.

To complete the electrical path for ablation energy, a reference electrode 152 is provided in the form of a flat plate contacting another surface of the anatomy portion 130. The reference electrode 152 is electrically connected by a cable 154 to the power source 136. Accordingly, an electrical circuit is completed from the ablation electrode 132 through the body portion 130 to the reference electrode 152. Consequently, the established electrical current flow heats the tissue causing a lesion as explained above. Again, as the electrode 132 is cooled, its temperature is limited and therefore as explained above, the tissue just beneath it will tend to remain relatively cool, and the lesion heat essentially is "thrown out" a distance from the electrode 132 and be effective for the volume of the loop 144. As somewhat apparent from the above, it should be recognized that electrodes with a variety of cooling agents, elements and structures can be utilized. In that regard, disclosed embodiments are exemplary, however, still other means for cooling an electrode tip are possible. For example, thermal electric cooling by the Seebeck effect may be used, where a solid state assembly within the tip of the electrode can be powered by electrical current and voltage from external apparatus, and this in turn can cause cooling of the agent or element within the tip. Cryogenic agents such as liquid nitrogen can be imagined to be flowed inside the electrode. Combined cryogenics, freezing with radio frequency heating can be considered as dual agents to alter and change the thermal distribution near the tip of the cooling device. Cooled gas may be injected into the electrode and heat carried away by forced convection as explained above.

It is to be noted that the cooling fluid, such as illustrated in the above examples may flow out from an electrode as by holes in the tip into the tissue or bodily region near the tip.

For example, if the tip were in blood, CSF, or other body or surgical fluid then the cooling fluid could be injected into that external region and not be returned through the electrodes to the source or controller as in the above examples. For example, if the electrode is in a surgical wound, then cooled saline could be sent out through the holes near the tip and thus cooling the tip and irrigating the surgical area. The cooled saline could be aspirated away from the heating site by other tubes, suction elements or channels which are not directly part of the electrode or heating structure.

Figure 7:
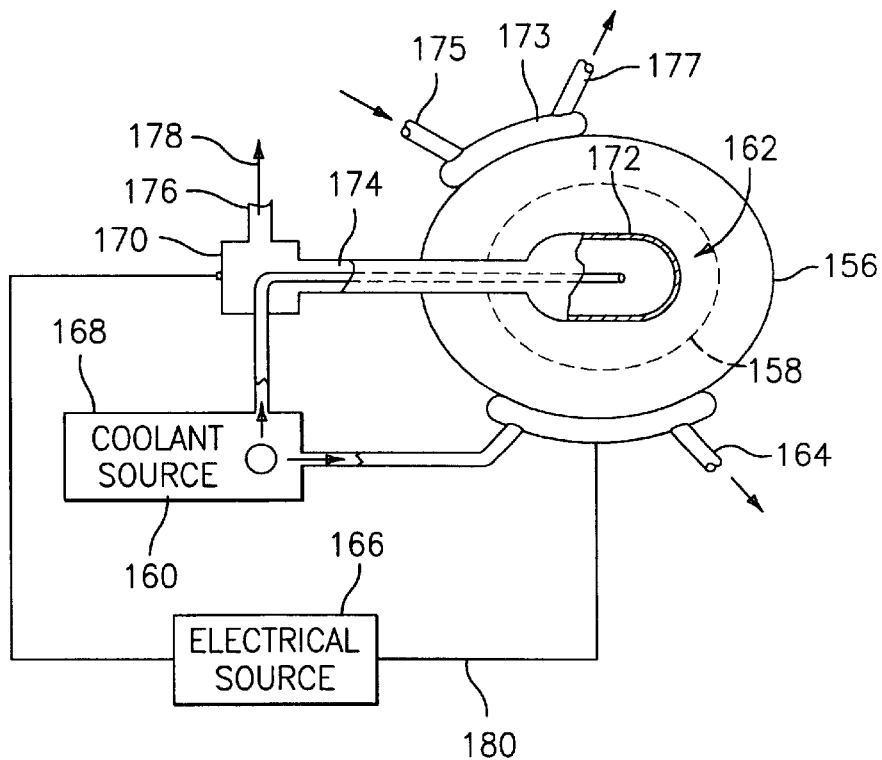
FIG. 7 is a diagrammatic illustration of a system in accordance herewith in still anther modified form hereof.

Referring next to FIG. 7, still another embodiment (again, not to scale) is represented, here in a form to treat a portion 156 of a patient's anatomy, specifically to ablate a volume designated by a dashed line 158. The system of FIG. 7 also involves surface-mounted electrodes and includes a coolant source 160 which supplies coolant to both an electrode structure 162 and a surface-mounted reference electrode 164. Additionally, electrical energy is provided from an electrical power source 166. Specifically supplied energy is through a cable 168 to a hub 170 which is electrically connected to the electrode structure 162. In that regard, the electrode structure 162 incorporates a balloon tip 172 (shown inflated or enlarged) as known in the art and which can expand within the portion 156 of body tissue. The surface of the tip 172 is conductive to deliver electric power to tissue in the case of an RF power source 166.

The hub 170 also incorporates fluid conduits including a passage 174 for supplying coolant to the balloon tip 172 from which fluid returns to exit from the hub as indicated at a port 176 and explained above, flow being in accordance with an arrow 178.

The electrical source 166 also is connected through a cable 180 establishing electrical contact with the reference electrode structure 164. Accordingly, both the electrode structures 164 and 162 receive coolant in accordance with the systems as described above. Another cooling element 173 is included to modify the overall thermal distribution. This element 173 may or may not have connection to the power source 166 and this may or may not serve to provide heating power but only impose a thermal boundary to control the extend or shape of the ablation volume. Ports 175 and 177 respectively receive and discharge coolant. Accordingly, further thermal boundary conditions may be provided within the body portion 130.

In the operation of the system of FIG. 7, electrical energy is supplied to the ablation electrode structure 162 emanating to the volume of the dashed line 158 to accomplish the desired ablation. Tissues near the electrode 164 are cooled and spared from the heating process. For example, if a RF ablation electrode is inserted into the prostate to treat a cancerous tumor, an inflatable cooled balloon, e.g. balloon tip 172 can be employed by insertion into the rectum in proximity to the rectal wall near the prostate and a cooled reference electrode 164 can be placed into the urethra. Alternatively, a cooled RF electrode can be placed in the urethra to preserve the integrity of the tissue walls of the urethra and the rectum during percutaneous or open electrode insertion into the prostate so as to ablate the prostate.

Another possible application of a cooling reference electrode is for use near to, in conjunction with, or combined with a secondary ablation electrode, would be in conjunction with heat ablation of tumors in the liver where a cooling electrode could be placed into one of the large vessels supplying the liver, with an RF electrode being placed within the tissue of the liver. Thus, the heating process can be delivered by the RF electrode and the cooling process or thermal boundary conditions can be imposed by the cooling electrode.

A similar situation can occur in the pancreas where an expandable RF ablation electrode, as the electrode structure 162, can be put into the pancreas duct and expanded against the tissue of the pancreas and the duct wall. Thus, the RF heating can throw the heat into the pancreas where a tumor or other anomaly may be present. At the same time, the electrode can have cooling circulation so that the tissue immediately adjacent to the electrode in the duct wall can be kept sufficiently cool that it is not destroyed. A ring of annular lesions made by RF heating can be done in this way, where an inner annulus can be spared heating and destruction, whereas smaller annuli, at larger radius from the electrode or the balloon or stent electrode can be thermally destroyed.

It is also possible that large cooled RF ablation electrodes, microwave electrodes, or laser ablation systems can be imposed on or placed in contact with the tissue of the surface of the body or on tissue inside the body such as in open surgical fields or in bodily cavities, vessels, which other reference or indifferent electrodes, cooled or not cooled, can be placed nearby or in a specific orientation relative to them.

As still another consideration, in accordance herewith, a variety of RF electrodes can be employed as explained above that are either electrically activated or inactive so as to set up specific thermal and electrical boundary conditions within tissue and to thereby spare regions of tissue from heat ablation while at the same time destroying other regions of tissue under the control of the configuration electrode and thermal elements and the operator.

As indicated above, a computer system may be effectively used as to calculate the thermal and electrical distribution and attain a desired thermo distribution within the tissue. In that regard, account is taken of thermo, convective and conductive properties of the tissue and fluids as well as Maxwell's equations to determine the density and the distribution of the tissue, all being considered by computer workstation and with a relevant graphics display.

Further in relation to graphics displays, in accordance herewith it may be useful to monitor real time or interactive images as from CT, MRI, PET, etc. in relation to the time-course and spacial distributions of thermo ablation. Controller means such as computers can predict and control the process of such heating. In that regard, CT and MRI imaging is sensitive to thermal effects and to tissue changes associated with RF heatings, and these can be monitored during or just after the heating process. For example, tissue necrosis edema break down of the blood brain barrier, etc. and thus is visible immediately or very soon after heat ablation. Such manifestations can be used to monitor the ablation size and to feedback and control the heating process. Such changes can be observed and monitored using computer graphics techniques.

Figure 8:
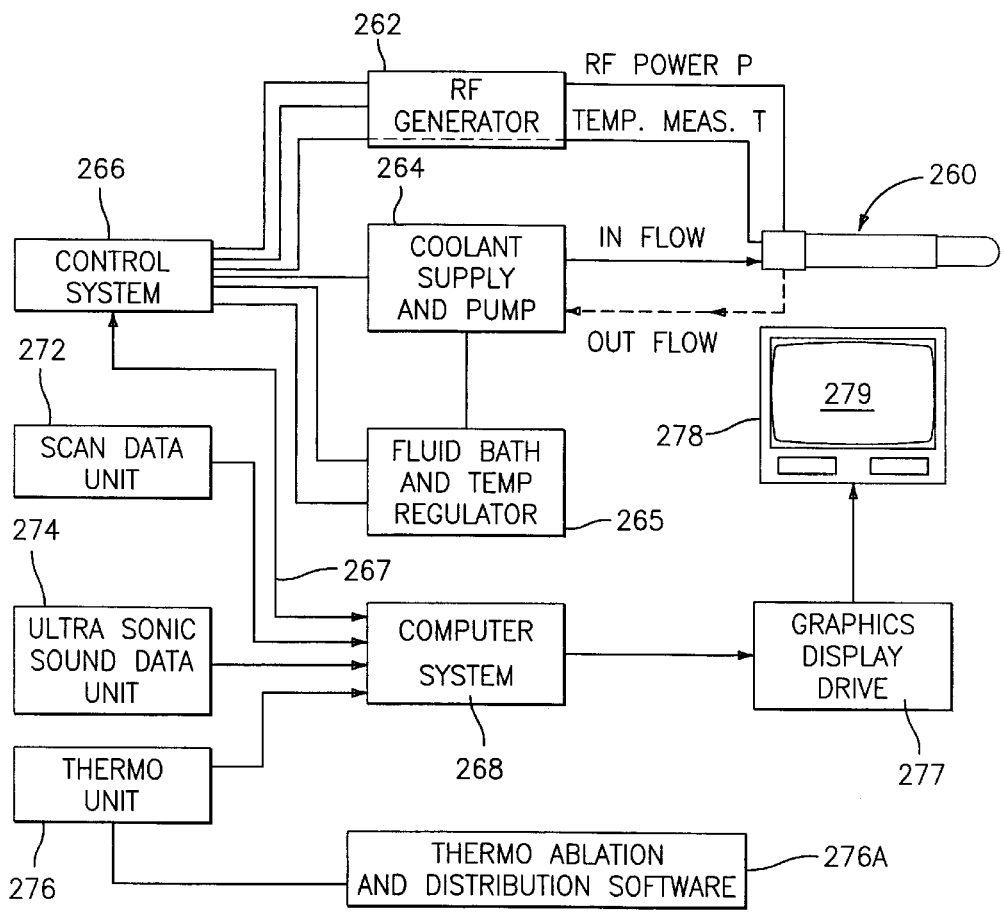
FIG. 8 is a block and schematic diagram of an extended embodiment of the system of the present invention.
Figure 10A:
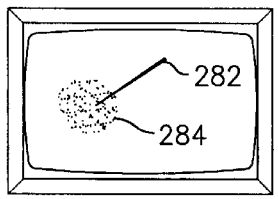
FIG. 10 is a pictorial view of exemplary displays by the system of FIG. 8.
Figure 10B:
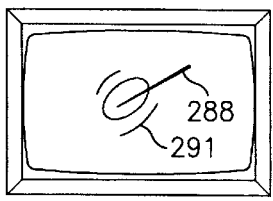
Figure 10C:
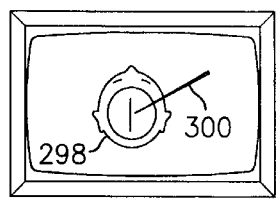
Figure 10D:
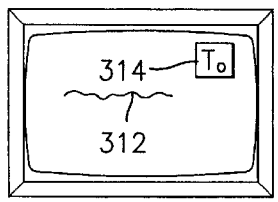
Figure 10E:
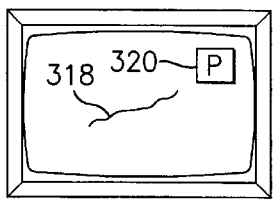
Figure 10F:
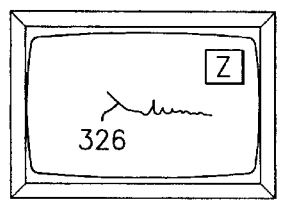

Next, consider embodiments of the system implemented with computer assisted control and also to provide graphics displays as with real-time components. Such an embodiment is shown in FIG. 8 and will now be described. Essentially, parameters of the situation are reduced to representative signals that are processed to provide displays. Computed data showing an electrode in a tissue environment may be combined with scanned image data (stored for example) to provide a variety of composite displays.

FIG. 8 shows an ablation electrode structure 260 (right) which may take any of multiple forms including the embodiments described above. The electrode structure 260 is energized by an RF generator 262 and cooled by coolant supplied from a source 264. A control system 266 (left)

regulates various parameters (energy and coolant flows) in accordance with a predetermined plan that is programmed into a computer system 268 (lower center). Note that various forms of feedback control systems are well known and satisfactory for implementation in the system 268. Specifically, the literature on feedback control systems is exceedingly well known as exemplified in the textbook, MODERN CONTROL ENGINEERING, by K. Ogata, Prentice-Hall, Englewood Cliffs, N.J., 1970.

Functionally, the computer system 268 receives parameters through a bus 267 from the control system 266 to in turn control and accomplish the desired program. That is, the computer system 268 implements a monitoring and feedback program with respect to the parameters attendant operation of the ablation structure 260. Such operations are accomplished through the bus 267 in accordance with well known data processing and control techniques.

A simple two-parameter control system can be implemented by the control system 266 in conjugation with the computer 268 and input data (units 272 and 274) involving a thermal distribution calculation by the computer 268 as illustrated. A look-up table or function generator defines the ablation volume, viz., length and width dimensions, as a function of the tip geometry and tip temperature. The tip temperature $T_0$ could be clamped at a fixed value by cooling fluid or if uncooled, the value $T_0$ is measured by thermosensors. Using tables such as described in the paper of Cosman, et al., entitled "Theoretical Aspects of Radiofrequency Lesions in the Dorsal Root Entry Zone," *Neurosurgery* 15:945–950, 1984, one could predict the width or minor diameter of the prolate ellipsoid of revolution which represents the ablation isotherm and corresponding to say a given power output level from the lesion generator at a given tip temperature near the electrode. This could either be derived empirically from experimental data or could be calculated from the equilibrium equation where:

K is the tissue thermal conductivity,

σ is the tissue electrical conductivity,

T is the temperature in the tissue, and $dQ_c/dt$ is the rate of heat loss due to blood circulation (taken from Cosman, et al., reference immediately above).

Therefore, the surface of revolution corresponding to the ablation temperature of approximately 50° C. could be determined as a functional equation, $$S(T_0, R_0, L_0, P_0, x, y, x) = 0$$

This might be the equation of a surface specifying the x,y,z coordinates relative to the tip of the electrode as a function of the tip radius parameter $R_0$, tip length $L_0$, the tip temperature $T_0$, and the power P of the RF lesion generator. This surface S could be displayed in the coordinate system of the electrode or in the 3D coordinate system of the CT or MR data or in a stereotactic coordinate system space referenced to a localizer structure, or localizer marker(s), or external apparatus (arc, frame, etc.) near the patient. The surface could be displayed on the computer as a red spheroid around the tip. Its relation to the defined lesion volume could be obvious by graphic rendering such as done for radiosurgery in the XKnife product of Radionics, Inc. of Burlington, Mass.

Figure 9:
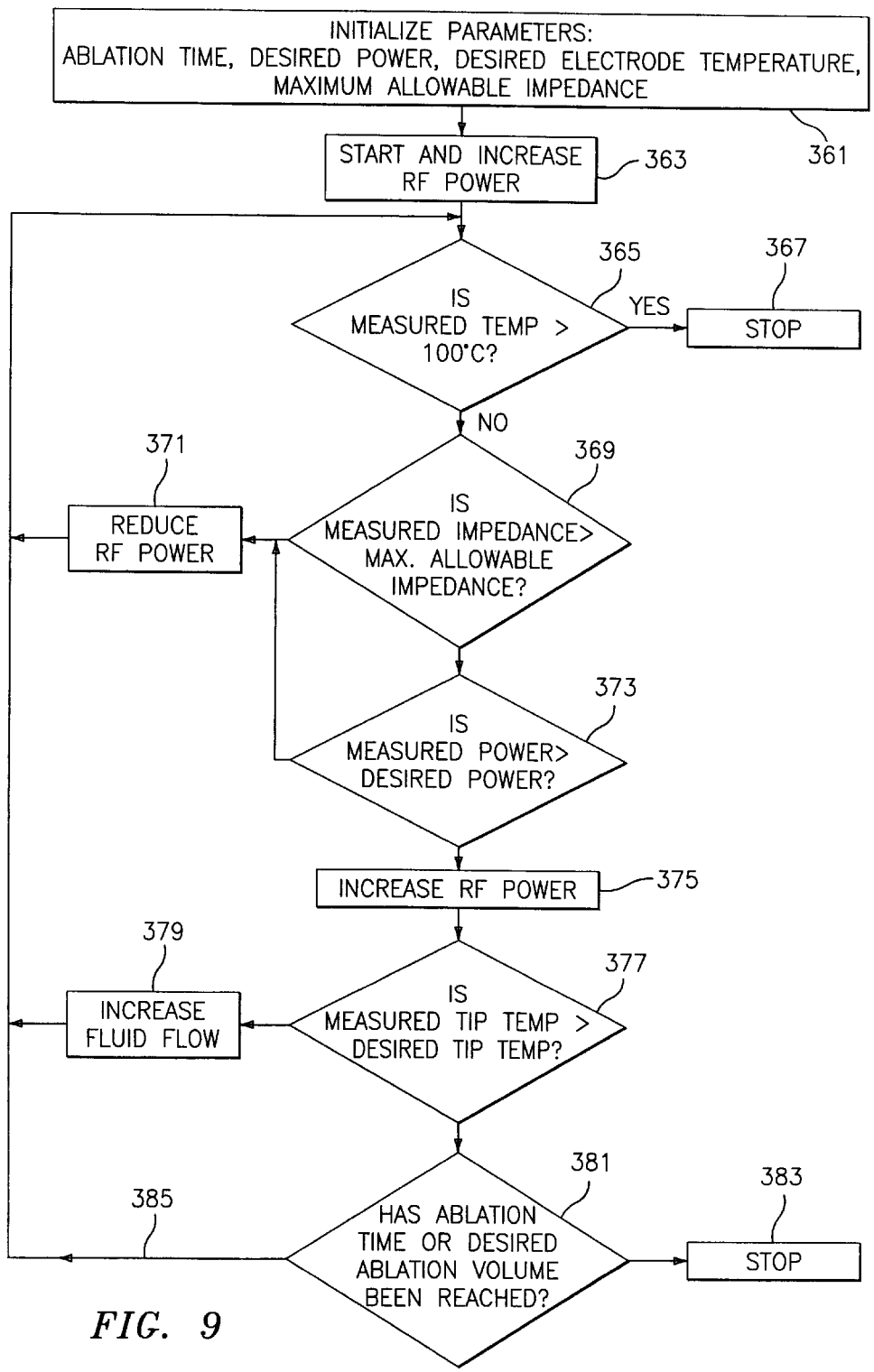
FIG. 9 is a computer program flow chart illustrating operations within the system of FIG. 8.

A simple specific illustrative program for implementation by the computer system 268 is illustrated in FIG. 9. Essentially, it depicts an initializing operation of setting parameters as indicated (block 361). Specifically, ablation time, power, electrode temperature, and allowable impedance are all initialized. Thereafter, the process is initiated with the established parameters as indicated by the block 363. From that stage, the data is monitored. Specifically, the temperature is measured as indicated in the various disclosed embodiments. As indicated by the query block 365, if a temperature in excess of 100° C. is measured, the procedure is terminated (block 367).

If temperatures are below the critical level, the maximum allowable impedance is next of concern. That is, as indicated by the query block 369, if the temperature is exceeded, the RF power is reduced, see block 371. In that regard note that temperature is indicated to be frequently checked in the program. In fact, the system may maintain a continual observation of temperature with an override to terminate the procedure at any time excessive values are observed. However, for illustrative purposes, the program is described in a step process.

With the establishment of acceptable levels of temperature and impedance (blocks 365 and 369) the power is measured with respect to the desired level (block 373). An excessive level again results in a power reduction (block 371), otherwise, if power is low, it is increased (block 375). Thus, power is adjusted to attain the desired level.

With the desired level of power established, the tip temperature is measured, as indicated by the block 377. An excessive level of tip temperature actuates an increase in the flow of coolant (block 379) and a check of the other parameters as indicated in FIG. 9. Otherwise, the final query is represented by a block 377, specifically, has the desired ablation volume been attained. If so, the procedure is terminate (block 383) otherwise, as indicated by the line 385, the operation is cycled, returning to the block 365.

Returning to the computer related representation of FIG. 8, the system also receives data from other sources, specifically a scan data unit 272, a sound data unit 274 and a remote temperature unit 276 operating with ablation and distribution software 276A. Accordingly, in addition to implementing a basic ablation control program, the computer system 268 provides raw display data to a graphics display drive 277 (image generator) for actuating a display unit 278. Thus, multiple displays are available on a screen 279, for example, slicings, time courses, reformattings, and digital subtraction representations, as well as digital and analog meter representations. Exemplary forms of displays are shown in FIG. 10 as will be treated at a later point.

With regard to data sources, the scan data unit 272 stores two or three dimensional graphics data relating to the surgery target to be provided selectively so that a surgeon may visualize the anatomy prior to, during and after the procedure. The data stored by the scan unit 272 may take the form of CT or MRI data developed prior to the surgical event as well known. The data may be either stereotactic or non stereotactic involving immobilizers, fiducial marks, graphic reference means and so on. Forms of such data and its processing are disclosed in U.S. Pat. No. 4,608,977, Brown, entitled System Using Computed Tomography As For Selective Body Treatment, Sep. 2, 1968. The literature of Radionics, Inc. of Burlington, Mass. also is relevant.

The sonic/ultrasound unit 274 may take a form well known in the art to provide sonic data, as from a stethoscope, electronic microphone or sonic detector to visualize tissue. For example, the data is provided and processed to display the electrode structure 260 with respect to anatomy. In that regard, signal represented data from the sonic data (unit 274) and the scan data (unit 272) may be combined by the computer system 268 to provide display signals for composite displays.

Various other displays may be provided to inform and guide the procedure as it is somewhat controlled with respect to the flows of energy and coolant. In that regard, the program may be implemented to include calculation algorithms, look-up tables, heuristic algorithms, historical clinical data, mathematical calculations involving field and thermal distribution calculations by finite element methods, analytical form solutions, computer theoretic methods, any or all of which may be used to preplan and variously control image data as well as operation procedures.

FIG. 10 illustrates exemplary displays that may be provided on the screen 279 in the operation of the embodiment of FIG. 10. A display 10A depicts a real time or preplanned trajectory of a probe path 282 indicating the course of an electrode tip into the body, specifically a tumor structure as represented by a cloud of dots 284. Note that CT contrast agents can be used to "see" the ablation volume during or following thermo surgery with the consequence that the display provides a direct view of the results immediately following the heating process.

Another screen display 10B, depicts a preplanned electrode path 290 in a slice 291 of a three-dimensional aspect of course, the slice 291 may be depicted on the basis of scanned data provided from the unit 272 (FIG. 8). Display of the electrode geometry (viz., tip length and diameter, and shape) can be given here as well as 3D or stereotactic views relative to other anatomy.

Another represented screen display 10C, shows a rendering 298 of a slice of patient anatomy with a path 300 depicted for a thermo surgical probe. Multiple electrode paths may be shown which are either parallel or non parallel, stereotactically placed or in various locations within the body.

In a display 10D, a graph line 312 is represented frozen in time or preplanned, for example indicating the thermo sensor readout of temperature sensors associated with the coolant fluid electrode tip, accessory probes or cooling or heating applicators, multiple sensor data, etc. as described previously. A digital display, designation, or multiple digital displays might be shown in a subwindow 314. Accordingly, various graphic curves might be shown, for example, a red curve might represent tissue temperature while a green curve represents fluid temperature and a yellow curve represents fluid temperature at another location. In such a format, an orange curve might represent tissue temperature as measured by a satellite electrode.

Considering a display 10E, a graph line 318 shows the output of the RF generator as a function of time. Concurrently, a subwindow 320 indicates a digital or analog representation of the instant power, current, voltage, or other power output or monitored ablation parameters.

In a display 10F, a curve 326 indicates the impedance of the electrode-structure circuit and the tissue being heated. Generally, an impedance drop is anticipated as tissue is heated with a rise of impedance if tissue charring or boiling is approached or reached; in that regard, see a paper of E. R. Cosman, et al. entitled "Radiofrequency Lesion Generation And Its Effects On Tissue Impedance", Applied Neurophysiology, 51:230–242, 1988. The system could give a control or indication of the extent of the ablation volume and safeguard against exceeding boiling and uncontrolled gas formation.

Figure 11:
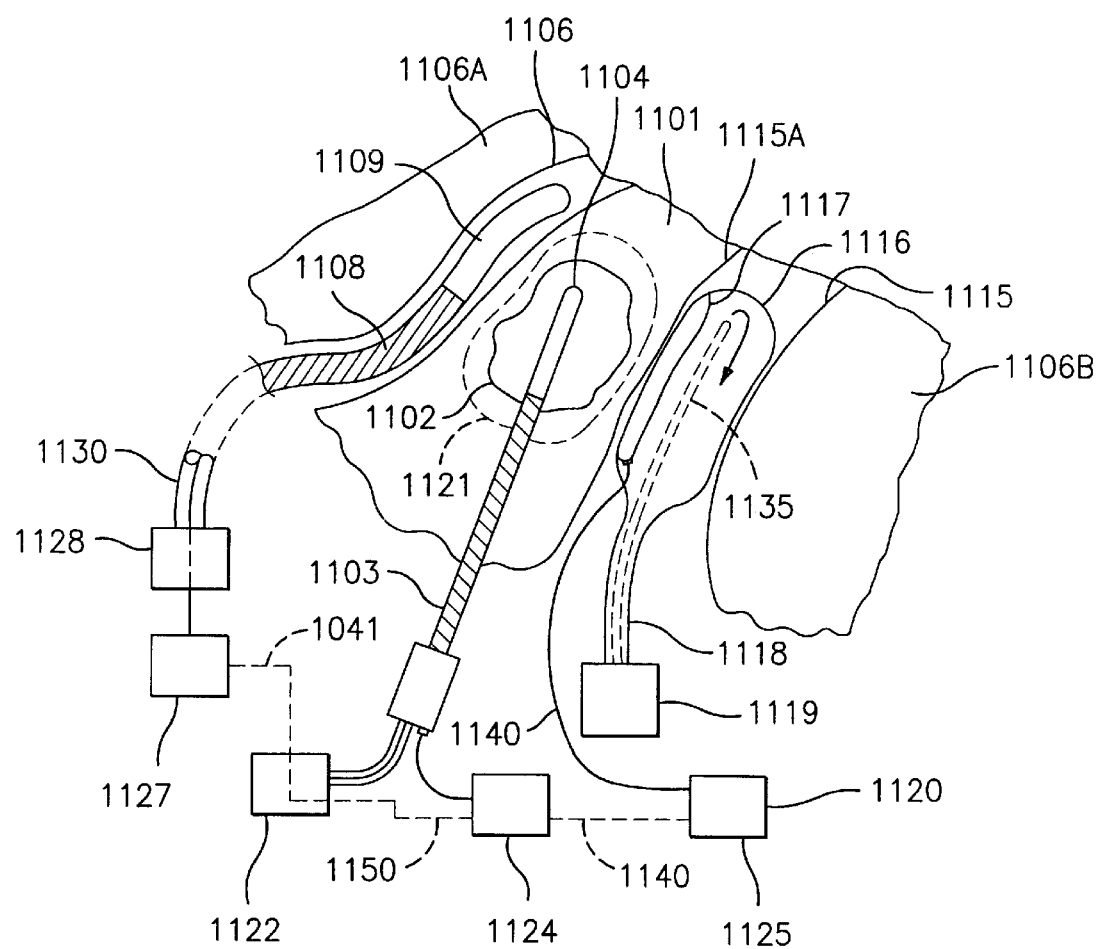
FIG. 11 is a sectional view illustrating an exemplary procedure utilizing a form of system of the present invention.

Referring now to FIG. 11, a compound embodiment is represented with respect to body tissues, shown as the regions marked by 1106A, 1101, and 1106B. Natural orifices or channels in the body are shown as 1106 and 1115. These channels may be external openings (viz. rectum, urethra, throat, bronchae, etc.) or may be internal channels (viz., blood vessels or duct ways, as the aorta, arterial or venous vessels, liver, pancreatic, etc. ducts or vessels, aqueducts of the liver, pancreas, kidney, or other organs, ventricular aqueducts in the brain, the intestines, throat, bronchae, etc.). Catheter type electrode 1109 is in channel 1106, and inflatable electrode 1117 has a surface against wall 1115A so as to be in electrical and/or thermal contact. Applicator electrode 1116 may be inflatable as a balloon or condom, and may be insulated over much of its surface, and internal coolant circulation by interior channels (as 1135). Tissue penetrating electrode 1103 is in the tissue region 1101, so its electrode tip 1104 is at a target volume represented by line 1102. The electrodes may have structures as described previously herein, and accordant heating supplies (as 1127, 1124, and 1120 which may be connected together or separate) and cooling supplies (as 1128, 1122, and 1119), as described herein. The power sources 1127, 1124, and 1120 may be RF sources, and they can be connected, as by lines 1140, 1150, and 1141, and be at different poles and varying phased relationships in time (as sequenced or phased arrays) between the electrode tips 1109, 1121, and 1117 to create various heating effects and different times and places. Each electrode may or may not have cooling supply (as 1128, 1122, and 1119) which may be inter-controlled, also with heating controls (as represented by dashed lines 1041, 1150, and 1140), and these all may be controlled by a computer (viz., in 1124); in that regard exemplified below. By use of proper cooling and electromagnetic boundary conditions between one or more electrodes, the ablation zone (as dashed line 1121) may engulf the target volume (viz., a tumor, as line 1102), and not destroy delicate tissues in channels 1106 and 1115 because they are kept cool. One, all, or more of such electrodes may be used, dependent on the clinical case.

An application is the prostate. The electrode 1109 may be a cooled catheter type electrode (also steerable as needed) in the urethra 1106, and 1116 may be a cooled probe in the rectum 1115. Electrode 1104 may pierce through the rectal wall into the prostate where a tumor (1102) has been seen by imaging. Appropriate electrode cooling provides an ablation zone (illustrated by 1121) to engulf the prostate tumor (viz., as line 1102), but not destroying delicate mucous membranes on wall 1115A of the rectum and urethra (as illustrated by 1106) or seminal vesicles (not shown). Simultaneous or post-ablation imaging can confirm or control the ablation extent.

Another application is the liver, pancreas, or kidney (tissue 1101 may represent these organs). Catheter electrode 1108 is inserted percutaneously through a vessel (viz. in the groin) or directly through the abdomen if the electrode is as in FIG. 1 so that electrode tip 1109 lies in a hepatic or pancreatic vessel and/or duct. A second electrode 1103 may be inserted so its tip 1104 lies in tumor 1102. Cooling tip 1109 spares the vessel or duct while tumor 1102 is ablated. In these examples, electrode 1116 may be also actively RF heated, and it may be inflatable or expandable as a balloon, condom, or a stent (a wire mesh flexible structure commonly used in medical practice and for instance sold by Cook, Inc.) to fill the channel 1115 and conform and contact the walls (viz. surface 1115A). Part of its surface 1117 may "throw" heat into the tumor and also be cooled to prevent damaging the duct so that the duct can continue to process normally biological material.

FIG. 11 may also depict the situation where passage 1115 is the colon, and electrode 1116 is inflated to press against the colon wall, and by cooling plus RF heating it enables ablation of a tumor (viz. volume 1102) in or near the colon wall without totally destroying the colon wall itself.

As well be apparent to those skilled in the art, the system may take many forms with the multitude of variations. However, recapitulating to some extent, note that various energy sources could be employed as alternatives to RF energy. As examples, the energy could take the form of microwave energy, an ultrasonic heater providing sonic waves into tissue or a direct power source. Also as indicated, heating could be directed by various shapes of structures or variously apertured structures.

Alternative electrodes may take the form of cannula with fiber optic channels to transmit laser light into the tissue for the generation of heat at a depth. Various geometries (curved or straight) of laser systems may be employed. As noted, one form of RF power supply may comprise the RFG-3C Lesion Generator as produced by Radionics, Inc., but other electrical power sources such as electrosurgical RF power supplies, bipolar cautery supplies, etc. could be used.

Also as indicated in disclosed embodiments, various graphics displays may be incorporated in accordance herewith along with the cooling system as disclosed. As indicated, various controls may be provided as for the cooling system and the heating system coordinated by observed phenomena as may be displayed.

As explained with respect to the disclosed embodiments, many variations of electrodes or body terminals are practical including tubular shafts, square shafts and so on. Flat electrodes, area electrodes, multiple electrodes, arrays of electrodes, electrodes with side-outlet or side-issued-tips, electrodes with balloon tips, expandable tips or conformable tips can be considered within the system. Electrodes with steerable tips and electrode shafts which can be conformed or shaped or that can be malleable can be considered within the system. Electrodes which are designed to be placed within the body tissue or on the surface of the body or within cavities within the bodies can be devised which are encompassed herewith. Electrodes may or may not have temperature sensors within them or near them, and for instance the ablation process can be done by supplying heating power and applicator cooling without temperature monitoring or control but merely using empirical parameters such as heating power and cooling fluid temperature/flow. In view of these considerations, and as will be appreciated by persons skilled in the art, implementations and systems should be considered broadly and with reference to the claims as set forth below.

What is claimed is:

1. An electrical structure for use with a source of electrical energy to ablate tissue in a living subject, the electrical structure comprising:

an elongated tissue-penetrating electrode including a thermal-conductive rigid tubular member with a closed distal end and defining an interior cavity extending from the closed distal end to a proximal end of the rigid tubular member, the rigid tubular member defining an external, electrically conductive surface, the elongated tissue-penetrating electrode further including an insulation layer disposed on the external, electrically conductive surface and defining an exposed portion of the external electrically conductive surface disposed at the distal end;

an electrical connection to provide electrical energy from the source of electrical energy to the external, electrically conductive surface;

a fluid conduit sized to extend into the interior cavity of the rigid tubular member and adapted to be connected to a source of coolant to supply coolant for cooling tissue contiguous to the exposed portion of the external, electrically conductive surface;

an extension tip having a closed distal end and defining an interior cavity extending from the closed distal end to a proximal end of the extension tip, the proximal end being mounted to the distal end of the tubular member and wherein the fluid conduit is sized to extend into the cavity of the extension tip;

a thermosensor disposed within the interior cavity of the extension tip adjacent the distal end of the extension tip for detecting a temperature; and an adjustable source of coolant for adaptively providing coolant to the fluid conduit according to the measured temperature.

2. The electrical structure according to claim 1 wherein the rigid tubular member is formed of metal.

3. The electrical structure according to claim 1 wherein the closed distal end is integral with the tubular member.

4. The electrical structure according to claim 1 further including:

a temperature sensor mounted proximate the exposed portion; and a temperature indicator coupled to the temperature sensor to display temperature.

5. The electrical structure according to claim 1 further including:

at least one satellite electrode connected to the source of electrical energy to establish secondary current flow.

6. The electrical structure according to claim 1, wherein the proximal end of the extension tip is slidably engaged with the distal end of the tubular member.

7. A system for targeting and ablating a predetermined volume of tissue to maximize the formation of a lesion, the electrical structure including:

an electrical energy generator;

an adjustable fluid source that adaptively provides coolant to a fluid conduit;

a hollow electrode formed with a continuous electrically and thermally conductive wall and having a closed distal end and an external surface in electrical communication with the electrical energy generator, the external surface having an insulation coating selectively applied thereto to define at least one electrical current conducting portion for establishing primary current flow adjacent the tissue to form the lesion, the electrode wall defining a sealed interior cavity;

a fluid conduit sized to extend into the interior cavity of the hollow electrode, the fluid conduit having a first end joined in fluid communication with the adjustable fluid source, and an opposite end connected in fluid communication with the electrode wall and having an open ended return line for connecting to the electrode wall to form a fluid exit path;

an extension tip having a closed distal end and defining an interior cavity extending from the closed distal end to a proximal end of the extension tip, the proximal end being mounted to the distal end of the hollow electrode, wherein the fluid conduit is sized to extend into the cavity of the extension tip; and a temperature sensor mounted proximate the distal end of the extension tip and generating an output signal representative of a temperature proximate the distal end of the extension tip, the adjustable fluid source adaptively providing coolant according to the measured temperature.

8. The system according to claim 7 wherein the hollow electrode is formed of metal.

9. The system according to claim 7 wherein the closed distal end is integral with the tubular member.

10. The system according to claim 7 and further including:
   at least one satellite electrode adapted to be connected to the source of electrical energy to establish secondary current flow.

11. The system according to claim 7 wherein the adjustable fluid source maintains the tissue contiguous to the electrically and thermally conductive wall at a temperature below 100° C.

12. The system according to claim 7 wherein the adjustable fluid source maintains the tissue contiguous to the electrically and thermally conductive wall at a temperature below 37° C.

13. The system according to claim 7 wherein the closed distal end of the hollow electrode is defined as a hemispherical shape.

14. The system according to claim 7 wherein the electrical energy generator comprises an RF power supply.

15. The system according to claim 7 wherein an electrical insulation material is disposed on the extension tip that prevents current flow to tissue contiguous the extension tip.

16. The system according to claim 7 further comprising a current conducting portion temperature sensor mounted proximate the current conducting portion and generating an output signal representative of a temperature proximate the current conducting portion, the adjustable fluid source adaptively providing coolant according to the temperature proximate the current conducting portion.

17. The system according to claim 7 wherein the proximal end of the extension tip is slidably engaged with the distal end of the tubular member.

* * * * *